United States Patent [19]
Greene

[11] 3,966,763
[45] June 29, 1976

[54] PROCESS FOR PRODUCING 2-PYRROLIDONE

[75] Inventor: Janice L. Greene, Chagrin Falls, Ohio

[73] Assignee: Standard Oil Company, Cleveland, Ohio

[22] Filed: June 30, 1975

[21] Appl. No.: 591,878

[52] U.S. Cl. ................................. 260/326.5 FN
[51] Int. Cl.$^2$ ................................. C07D 207/26
[58] Field of Search .................... 260/326.5 FN

[56] References Cited
UNITED STATES PATENTS

| | | | |
|---|---|---|---|
| 3,095,423 | 6/1963 | Copenhaven et al. | 260/326.5 FN |
| 3,644,402 | 2/1972 | Takagi et al. | 260/326.5 FN |
| 3,781,298 | 12/1973 | Davis | 260/326.5 FN |

*Primary Examiner*—Alton D. Rollins
*Assistant Examiner*—Mary Vaughn
*Attorney, Agent, or Firm*—Evelyn R. Kosman; Herbert D. Knudsen; Larry W. Evans

[57] ABSTRACT

A process for producing 2-pyrrolidone by the simultaneous hydrolysis and hydrogenation of succinonitrile at elevated temperatures and pressures in the presence of a hydrogenation catalyst and a reaction promoter selected from the group consisting of 2-pyrrolidone and N-alkyl-2-pyrrolidone wherein the alkyl group contains from 1 to 6 carbon atoms.

9 Claims, No Drawings

PROCESS FOR PRODUCING 2-PYRROLIDONE

This invention relates to an improved process for the synthesis of 2-pyrrolidone (also known as 2-pyrrolidinone) from succinonitrile. More particularly this invention relates to the synthesis of 2-pyrrolidone by the simultaneous hydrolysis and hydrogenation of succinonitrile in the presence of a hydrogenation catalyst and a reaction promoter such as added pyrrolidone and an N-alkyl-2-pyrrolidone.

BACKGROUND OF THE INVENTION

Pyrrolidone is particularly useful as an intermediate in the preparation of Nylon-4, in the preparation of N-methyl pyrrolidone and N-vinyl pyrrolidone which is useful as organic solvents, and in the formation of polymers which have certain specific properties.

Pyrrolidone has been prepared according to U.S. Pat. No. 3,095,423 in a liquid phase process comprising the simultaneous hydrogenation and hydrolysis of succinonitrile utilizing aqueous ammonia and hydrogen pressures of at least 500 psi, and preferably hydrogen pressures of from 1000–2000 psi. U.S. Pat. No. 3,781,298 also describes a single step process for preparing 2-pyrrolidone by hydrogenating succinonitrile in an aqueous solution but at pressures greater than 2000 psig. U.S. Pat. No. 3,644,402 discloses a two-step process for hydrolyzing and hydrogenating succinonitrile sequentially, wherein the hydrolysis reaction if conducted in aqueous ammonia and the hydrogenation in the presence of a nitrogen-containing basic organic solvent at pressures of from about 750 to 3000 psi.

SUMMARY OF THE INVENTION

According to the present invention, it has been discovered that improved yields of 2-pyrrolidone can be obtained by contacting an aqueous reaction mixture of succinonitrile with hydrogen at elevated temperatures and pressures in the presence of hydrogenation catalyst, by adding to the aqueous reaction mixture a reaction promoter selected from the group consisting of 2-pyrrolidone and the N-alkyl-2-pyrrolidones wherein the alkyl group contains from 1 to 6 carbon atoms. The overall reaction taking place in this process may be represented by the following equation:

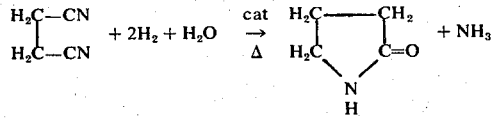

It is surprising that substantially higher conversions and yields of 2-pyrrolidone are obtained in this reaction in the presence of added pyrrolidone in view of the desirability of maintaining low levels of pyrrolidone in the aqueous reaction mixture so as to minimize the formation of undesirable polymer.

Improved conversions to pyrrolidone are observed by adding to the reaction mixture promoters such as 2-pyrrolidone per se, an N-alkyl-2-pyrrolidone or a previous product mixture containing 2-pyrrolidone. The concentration of the added promoter may vary widely, but concentrations ranging from about 0.1 to 1.5 moles per mole of succinonitrile are preferred, while concentrations of from 0.3 to 1.0 moles per mole of succinonitrile are most preferred.

The preferred reaction promoter in this process is 2-pyrrolidone for the reason that problems associated with its recycle and recovery are minimized. Also, especially desirable is the use of N-methylpyrrolidone.

The catalyst employed in this process can be any hydrogenation catalyst. Preferred catalysts are chosen from the group of hydrogenation catalysts containing the elements of nickel, chromium, platinum, palladium, rhodium, ruthenium, cobalt, copper and rhenium. The catalysts may take any form, for example, the catalysts may be oxides, metals or Raney catalysts. They may be supported catalysts wherein the supporting medium may be carbon, alumina, silica, silica-alumina, zirconia, kieselguhr, or other well-known inert supports.

The amount of hydrogenation catalyst used may also vary widely, and normally from about 0.1 to 40 percent by weight is used based on the weight of succinonitrile employed in the reaction. However, it is more preferable to use from about 3.5 to 35 weight percent catalyst based on the weight of the succinonitrile reacted. The catalyst may be conveniently recovered from the reaction mixture by filtration or decantation and can be reused in subsequent reactions, normally without regeneration.

The ratio of the reactants—succinonitrile, water and hydrogen—charged to the reactor in this process are not critical. Water can be present in stoichiometric amounts, i.e., one mole of water/mole of succinonitrile, or excess water may be used. Generally, it is preferred to employ from about 5–25 moles of water per mole of succinonitrile. The upper limit of the amount of water used is governed by the excessive hydrolysis of succinonitrile to succinimide and by the economics of product recovery, and the lower limit is governed by polymer formation.

While the reaction may be carried out using hydrogen pressures ranging from about 100 to 1500 psi, one of the more important advantages associated with this process is that optimum results are obtained at much lower hydrogen pressures than are employed in processes of the prior art. The use of lower hydrogenation pressures in the instant process minimizes the excessive hydrogenation of succinonitrile to pyrrolidine and related products, and it has an important economic significance particularly in the need for less expensive reactor equipment. Preferably hydrogen pressures of about 300 to 750 psi are utilized.

The process of this invention may be conducted using various techniques and reactors, and both batch-type and continuous operations are contemplated. Additionally, recycle of the reaction product to the reaction mixture is beneficial to the reaction. In a preferred preparation, water, succinonitrile, the promoter and catalyst are charged to a reactor in the desired concentrations and the reactor is then closed and further charged with hydrogen. The temperature of the reaction mixture is then raised to the level desired, with stirring. The reaction temperature may range from about 50° to 300°C, but preferably temperature within the range of from about 100° to 200°C are employed. The reaction is continued at the desired temperature for a period of time ranging from about 0.5 to 6 hours, however, with continuous operation contact time may be as low as 0.1 hours. Generally, the reaction time is within the range of from about 2 to 5 hours, after which time the heat is removed, and the reaction mass is allowed to cool. The reaction mixture is then filtered to remove the catalyst and flash distilled to remove excess water and volatile components. The product, 2-pyrrolidone, is then recovered in good yields by fractional distillation of the remaining reaction mixture.

SPECIFIC EMBODIMENTS

Comparative Examples A-C and Examples 1-7 - Comparisons of Promoted and Unpromoted Reactions.

Comparative Examples A–C

The reaction in each comparative example was carried out by placing deionized water, succinonitrile and a hydrogenation catalyst in a one-liter, stainless steel Parr autoclave. The autoclave was flushed with nitrogen for 5 minutes, and with stirring was pressured to 200 psig. with nitrogen and checked for leakage by increasing the nitrogen pressure to twice that of the working pressure for a period of 15 minutes. When no leaks were detected the nitrogen was vented, the autoclave heated to 60°C for a half hour, the pressured with hydrogen to the working pressure. As hydrogen was consumed, hydrogen was added from time to time to maintain the working pressure. Stirring and heating were continued for about one hour after the hydrogen addition and before the reaction temperature of 140°C was reached. The exothermic reaction often carried the reaction temperature higher as indicated in Tables 1 & 2. Periodically, samples were removed from the autoclave and were analyzed by gas-liquid chromatography for unreacted succinonitrile, pyrrolidone and the hydrolysis products, succinimide and succinic acid. The conditions under which the maximum pyrrolidone conversion was observed were then recorded. At that time the succinonitrile conversion was usually complete. Other by-products identified in addition to succinimide and succinic acid were pyrrolidine and butyrolactone. The reaction contents were then cooled, filtered, and concentrated by vacuum stripping.

EXAMPLES 1–7

The experimental procedure employed in the comparative Examples A-C was repeated in examples 1-7 with the exception that a reaction promoter was added to the reaction mixture of water, succinonitrile and catalyst in the concentrations indicated. In examples 1-7, the promoters 2-pyrrolidone and N-methyl 2-pyrrolidone were added to the reaction mixtures, and these examples are representative of the present invention. In example 3, reaction promoter 2-pyrrolidone was incorporated into the reaction mixture by adding the reaction product of comparative example C in amounts to give the equivalent concentration of 0.5 moles of 2-pyrrolidone per mole of succinonitrile.

The effectiveness of 2-pyrrolidone and the N-alkyl-2-pyrrolidones as reaction promoters for the reaction of this invention is demonstrated by the examples in Tables 1 & 2. It is also demonstrated by these examples that the increased conversions to 2-pyrrolidone observed with these promoters occurs with various hydrogenation catalysts and at various reaction conditions and reactant ratios. Example 3 demonstrates that the use of a product mixture containing 2-pyrrolidone as a promoter is as effective in increasing the conversion of succinonitrile to pyrrolidone as is the addition of 2-pyrrolidone per se. Thus recycle of the product mixture is beneficial to the reaction.

Table 1

Effect of 2-Pyrrolidone and N—Methyl Pyrrolidone as Reaction Promoters on Conversion of Succinonitrile to 2-Pyrrolidone Reactant Ratios
Moles of water/mole succinonitrile = 20
Moles of promoter/mole succinonitrile = 0.5
Hydrogen pressure, psig. = 450

| Example | Promoter | Catalyst | Grams Catalyst/ Mole SN | Reaction Conditions Temp., °C | Time, Hours | Net Mole % Conversion to Pyrrolidone |
|---|---|---|---|---|---|---|
| Comp. A | None | Nickel Boride | 3 | 140 | 6.7 | 37.4 |
| 1 | 2-pyrrolidone | Nickel Boride | 3 | 144 | 4.9 | 54.9 |
| Comp. B | None | Raney Nickel | 25 | 145 | 4.0 | 31 |
| 2 | N—Methyl-2-Pyrrolidone* | Raney Nickel | 25 | 141 | 2.0 | 44 |
| Comp. C | None | Nickel Boride | 9 | 144 | 7.1 | 42.9 |
| 3 | 2-pyrrolidone (recycled) | Nickel Boride | 9 | 145 | 7.0 | 55.9 |

*Moles of Promoter/Mole SN = 0.4

Table 2

Conversion of Succinonitrile to 2-Pyrrolidone Under Various Reaction Conditions

| Example | Reaction Promoter, 2-Pyrrolidone Moles/Mole S.N. | Catalyst | Grams/ Mole SN | Moles H₂O/ Mole SN | Reaction Conditions H₂ Press. psig. | Temp. °C | Reaction Time, Hrs. | Net Mole % Conversion to 2-Pyrrolidone |
|---|---|---|---|---|---|---|---|---|
| 4 | 1.0 | Nickel Boride | 3 | 25 | 450 | 140 | 3.5 | 55.2 |
| 5 | 0.5 | Nickel Boride | 3 | 10 | 450 | 138 | 4.4 | 43.4 |
| 6 | 0.5 | Nickel Boride | 3 | 20 | 350 | 135 | 3.0 | 38.2 |
| 7 | 0.5 | Nickel Boride | 3 | 20 | 750 | 140 | 3.2 | 38 |

I claim:

1. In the process for producing 2-pyrrolidone by contacting an aqueous reaction mixture of succinonitrile with hydrogen at elevated temperatures and pressures in the presence of a hydrogenation catalyst, the improvement comprising:
   adding to the aqueous reaction mixture a reaction promoter selected from the group consisting of 2-pyrrolidone and an N-alkyl-2-pyrrolidone wherein the alkyl group contains from 1 to 6 carbon atoms.

2. The process in claim 1 wherein the promoter is 2-pyrrolidone.

3. The process in claim 2 wherein the reaction promoter 2-pyrrolidone is added in the form of a reaction product mixture obtained from a previous reaction.

4. The process in claim 1 wherein the promoter is N-methyl-2-pyrrolidone.

5. The process in claim 1 wherein the reaction promoter is added to the reaction mixture in a concentration within the range of from about 0.1 to 1.5 moles per mole of succinonitrile.

6. The process in claim 5 wherein the hydrogenation catalyst is a nickel-containing catalyst.

7. The process in claim 6 wherein the concentration of succinonitrile in the aqueous reaction medium is within the molar ratio of water to succinonitrile of from 5:1 to 25:1, and the catalyst is present in a concentration within the range of from 0.1 to 40 grams per gram mole of succinonitrile.

8. The process in claim 7 wherein the reaction temperature is within the range of from 50° to 300°C.

9. The process in claim 8 wherein the hydrogen pressure is within the range of from 100 to 1500 psi.

* * * * *